US 7,777,496 B2

| (12) | United States Patent | (10) Patent No.: | US 7,777,496 B2 |
|---|---|---|---|
| | Evans et al. | (45) Date of Patent: | Aug. 17, 2010 |

(54) REMOTE SENSOR SYSTEM FOR MONITORING THE CONDITION OF EARTHEN STRUCTURE AND METHOD OF ITS USE

(75) Inventors: James A. Evans, Tallulah, LA (US);
Joseph B. Dunbar, Vicksburg, MS (US);
George L. Mason, Vicksburg, MS (US);
Richard W. Haskins, Raymond, MS (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 232 days.

(21) Appl. No.: 12/175,645

(22) Filed: Jul. 18, 2008

(65) Prior Publication Data

US 2010/0013497 A1    Jan. 21, 2010

(51) Int. Cl.
*G01R 31/11* (2006.01)
(52) U.S. Cl. ..................... 324/534; 324/642
(58) Field of Classification Search ......... 324/532–534, 324/642
See application file for complete search history.

(56) References Cited

U.S. PATENT DOCUMENTS

| 4,415,885 | A | | 11/1983 | Mongeon |
| 4,571,578 | A | | 2/1986 | Karas |
| 4,812,645 | A | | 3/1989 | Griffiths |
| 4,927,232 | A | | 5/1990 | Griffiths |
| 4,930,852 | A | | 6/1990 | Wheeler et al. |
| 5,155,439 | A | * | 10/1992 | Holmbo et al. ............. 324/534 |
| 5,446,446 | A | | 8/1995 | Harman |
| 5,614,893 | A | | 3/1997 | Ahmad et al. |
| 5,705,984 | A | | 1/1998 | Wilson |
| 5,903,221 | A | | 5/1999 | Eslambulchi et al. |
| 6,181,841 | B1 | | 1/2001 | Hodge |
| 6,271,754 | B1 | | 8/2001 | Durtler |
| 6,288,640 | B1 | | 9/2001 | Gagnon |
| 6,487,914 | B1 | | 12/2002 | Hodge |
| 6,526,189 | B1 | | 2/2003 | Yankielun |
| 6,530,284 | B1 | | 3/2003 | Tambo et al. |

(Continued)

OTHER PUBLICATIONS

Bahar, Ezekiel, J. D. Saylor; A Feasibility Study to Monitor Soil Moisture Content Using Microwave Signals; IEEE Trans. on Microwave Theory & Tech.: vol. MTT-31, No. 7, Jul. 1983.

*Primary Examiner*—Vincent Q Nguyen
(74) *Attorney, Agent, or Firm*—Earl H. Baugher, Jr.

(57) ABSTRACT

A system and associated method permit remote monitoring of subsurface structure for purposes of early detection and location of hidden anomalies, e.g., water seepage in levees. Anomalies may be due to sand boils or displacement of underlying soil. Representative systems provide continuous monitoring via two complementary means: parallel pairs of ported (leaky) coaxial cables and a fiber optic cable, each pair of coaxial cables associated with a fiber optic cable. A fiber optic system, with associated light source, processor and display, together with an RF system, provides data to a remote location via telemetry or cellular phone, or both. The fiber optic cable(s) allow monitoring of displacement and vibrations within the structure. The ported coaxial cables, with associated RF source, using the same processor, display and telemetry used with the fiber optic sub-system, provide data for monitoring moisture change correlated to changes in the dielectric constant of surrounding material.

29 Claims, 9 Drawing Sheets

U.S. PATENT DOCUMENTS

| | | |
|---|---|---|
| 6,549,012 B2 | 4/2003 | Stolarczyk |
| 6,608,489 B2 | 8/2003 | Yankielun et al. |
| 6,648,552 B1 | 11/2003 | Smith et al. |
| 6,696,974 B1 | 2/2004 | Mathis |
| 6,909,669 B1 | 6/2005 | Yankielun et al. |
| 6,948,882 B2 | 9/2005 | Smith et al. |
| 7,141,815 B2 | 11/2006 | Yankielun |
| 2002/0130667 A1* | 9/2002 | Noe .......................... 324/534 |

* cited by examiner

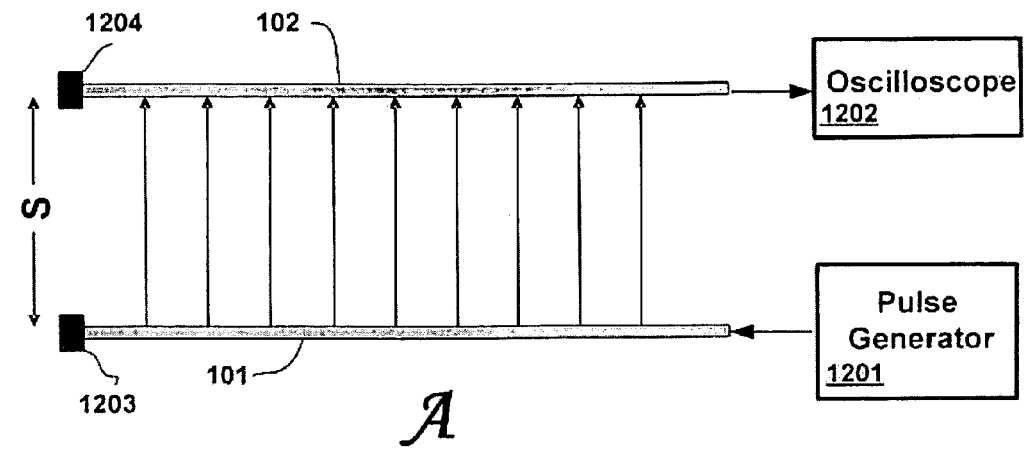
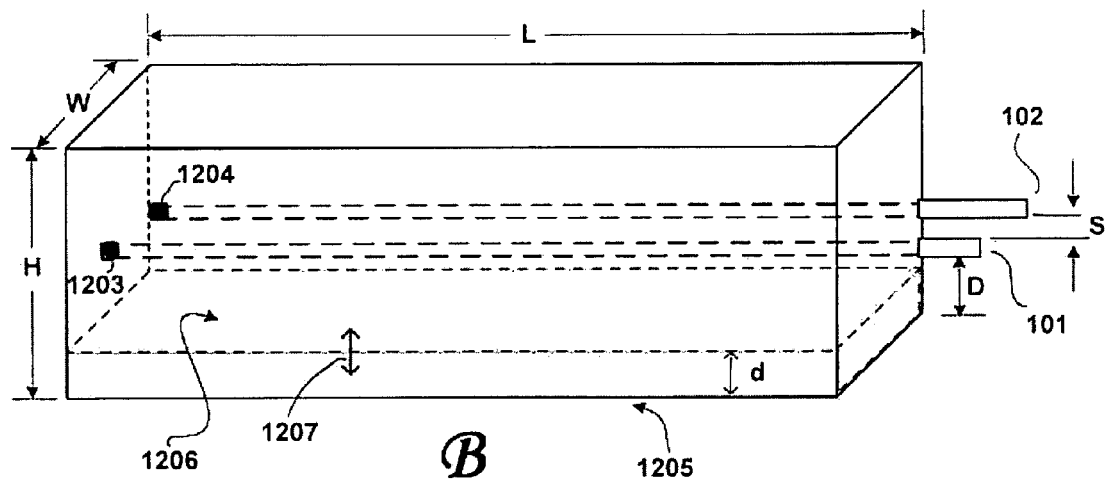
Fig. 12

REMOTE SENSOR SYSTEM FOR MONITORING THE CONDITION OF EARTHEN STRUCTURE AND METHOD OF ITS USE

STATEMENT OF GOVERNMENT INTEREST

Under paragraph 1(a) of Executive Order 10096, the conditions under which this invention was made entitle the Government of the United States, as represented by the Secretary of the Army, to an undivided interest therein on any patent granted thereon by the United States. This and related patents are available for licensing to qualified licensees. Please contact Phillip Stewart at 601 634-4113.

BACKGROUND

Dams and levees are built to contain waters and earthen levees are generally constructed using soils extracted nearby and vary in permeability and strength. Failure may be due to seepage, piping-dislocation, and subtle movement due to inadequate design, poor maintenance or excessive hydraulic loads.

Levees and dams are built with a factor of safety based on their size, expected height and rate of flow (flow nets) of water through the permeable soils of which they are constructed. The high flow line is a function of the dimensions of the levee and is part of the safety design factor. Detection in movement of the flow line may indicate seepage in the levee or dam. Prior warning of failure is usually unavailable until sand boils, major deformation, or both, are observed. It would be advantageous to identify minor movement, measurement of vibrations, or both in these structures before catastrophic failure. Several conventional methods are used to detect weakness. The first is to take many soil samples from "suspect" areas and ascertain sand content. This is expensive, labor intensive, and marginally effective. Other methods involving visual inspection during both dry and wet weather periods are less than satisfactory. Further, these methods do not provide continuous monitoring. Technical methods such as the use of ground-penetrating radar are limited by the small size of the sand channel and moisture content within the outer surface being surveyed. Externally applied electromagnetic fields (EMF) have low resolution, inadequate depth of penetration and produce target ambiguities and concomitant difficulty in data interpretation.

Accordingly there is a need for monitoring these structures, either continuously or at pre-specified intervals, to provide real time or near real time status on structural condition, often established by comparing change in both soil saturation levels and soil displacement along the structure.

BRIEF DESCRIPTION OF DRAWINGS

FIG. 12 depicts top and profile views of a test setup used in testing an embodiment of the present invention.

FIG. 13 is a cross section taken longitudinally of a specialized F.O. cable that may be used in select embodiments of the present invention.

DETAILED DESCRIPTION

Figure 1:
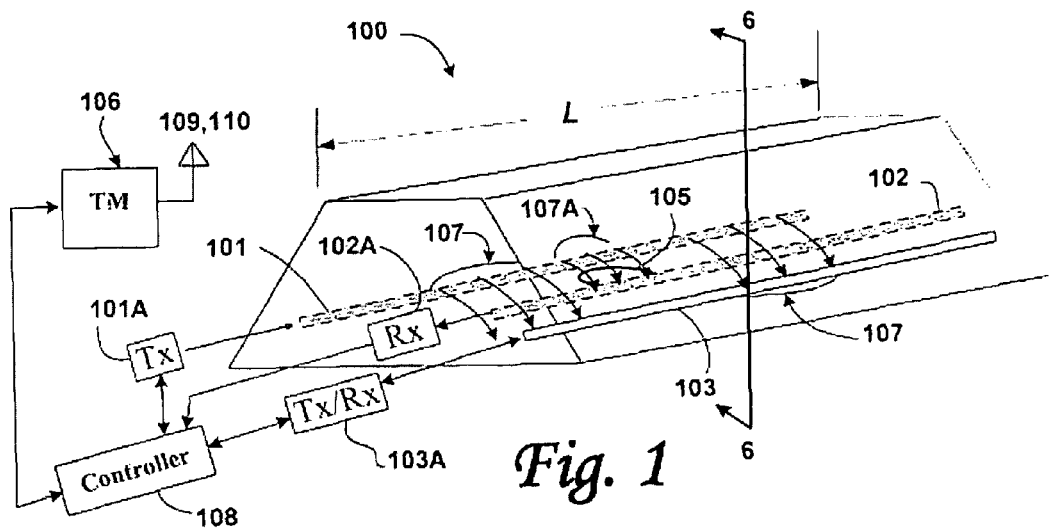
FIG. 1 is a simplified line drawing of an embodiment of the present invention as may be, incorporated into a levee.

Select embodiments of the present invention provide remote monitoring of subsurface structure in which an embodiment of the present invention has been installed. Select embodiments of the present invention provide early warning of irregularities or anomalies, continually monitoring structural integrity via pairs of ported (leaky) coaxial cables suitable for handling RF signals and one or more F.O. cables. The ported coaxial cables, one "transmitter" cable and one "receiver" cable in each pair, are used to detect and locate changes in the dielectric constant of material surrounding the cables. For example, water seepage into an earthen levee causes a change in moisture content of the soil that is reflected as a change in the dielectric constant of the material between the two ported coaxial cables of a pair. F.O. cables are employed to detect physical characteristics of a different nature than those detected by the ported coaxial cables. Examples include anomalies not necessarily evidenced by moisture intrusion, e.g., displacement of soil that may be due to remotely located sand boils, erosion or like causes, the displacement not associated with a change in the dielectric constant of the material adjacent the ported coaxial cables. Of course, both the ported coaxial cables and the F.O. cables are characterized upon initial installation to provide a baseline for taking comparative measurements over a long term.

Thus, in select embodiments of the present invention, one or more F.O. cables monitor displacement and vibrations and pairs of ported coaxial cables monitor changes in dielectric constant of material surrounding the ported coaxial cables. The combination also provides precise location of moisture changes and soil movement within the structure due to the anomalies. The F.O. cable(s) allow for continuous measurement of internal vibration and material displacement via Optical Time Domain Reflectometry (TDR), correlating time to distance and amplitude over time to relative displacement of material, while the ported coaxial cables employ "metallic" TDR to locate areas of change in dielectric constant of the soil.

Select embodiments of the present invention also provide a method of detecting subsurface anomalies in a structure employed to protect property from water ingress, e.g., levees, dams, and the like. For select embodiments of the present invention, the method comprises: (a) installing within the structure one or more pairs of ported transmitter coaxial cables, a first ported cable of each pair for transmitting electromagnetic signals, preferably at one or more radio frequencies (RF) and the second ported coaxial cable in parallel to each ported transmitter coaxial cable for receiving the transmitted signal from its paired transmitter ported coaxial cable: c) installing one or more F/O cables within the structure, e.g., in some embodiments of the present invention the F.O. cable is wound about either a ported transmitter coaxial cable or a ported receiver coaxial cable to facilitate installation via known techniques such as directional drilling; (d) illuminating the fiber optical cable, preferably with white light, and receiving reflected and refracted light with an optical receiver to detect and identify changes in refraction of light that indicate displacement of portions of the structure, (e) transmitting an electromagnetic signal, preferably an RF signal, along the ported transmitter coaxial cable of sufficient strength to be received by its "paired" ported receiver coaxial cable, such that the signal propagates through the surrounding material in the structure and induces an electromagnetic signal of sufficient strength to be propagated in the paired ported receiver coaxial cable, the characteristics of the ported coaxial cables further selected to optimize a pre-specified impedance match between at least the ported coaxial cables and surrounding material; (f) receiving the transmitted electromagnetic signal at the paired ported receiver coaxial cable, the signal of sufficient strength to propagate along the paired ported receiver coaxial cable to a receiver for processing the received electromagnetic signal with possible assistance of an amplifier incorporated in the paired receiver coaxial cable, the paired transmitter coaxial cable, or both: (g) processing the received RF and optical signals as data; h) analyzing and displaying the processed data to determine the location and amplitude of anomalies within the structure and (i) monitoring the received electromagnetic signal to detect change, wherein said monitoring is automated. Further, select embodiments of the present invention may provide an automated alarm when an anomaly reaches a pre-specified threshold.

In select embodiments of the present invention, a system simultaneously employs complementary techniques to detect and locate hidden anomalies in structure. The system comprises an RF sub-system comprising one or more pairs of transmitter and receiver ported coaxial cables; one or more RF sources directly energizing the transmitter ported coaxial cable(s), such that each RF source provides at least one analog signal; and one or more RF receivers communicating with each receiver ported coaxial cable, such that each RF receiver receives the analog signal leaked from ports of the transmitter cable as provided by the receiver cable; and an optics sub-system comprising: one or more fiber optical cables; one or more optical transceivers communicating with each fiber optic cable; such that the optical transceiver provides a analog optical signal and receives reflections of that analog signal from the fiber optic cable(s); and a control sub-system operating the RF sub-system and the optical sub-system, the control sub-system communicating with each of the RF and optical sub-systems, the control system comprising: one or more processors; one or more displays communicating with the processor(s); one or more I/O devices communicating with the processor(s) and the display(s); and one or more communications devices communicating with one or more of the I/O devices.

In select embodiments of the present invention, the system incorporates an alarm communicating with the control sub-system.

In select embodiments of the present invention, the communications apparatus further comprises a telemetry, sub-system communicating with the control sub-system that may include one or more cellular phones.

In select embodiments of the present invention, the RF sub-system incorporates a TDR system communicating with the control sub-system.

In select embodiments of the present invention, the RF TDR system communicates with the processor and the TDR system incorporates one or more RF signal generators for providing an analog signal to the ported transmission cable(s); an RF coupler couples the RF signal generator(s) to the transmitting ported transmission cable(s) and couples a synchronization signal to the receiving ported cable. A first algorithm processes the leakage signals on the processor, providing results of the processing to a display.

In select embodiments of the present invention, optical sub-system incorporates an OTDR system communicating with the control sub-system. In select embodiments of the present invention the OTDR comprises one or more first amplifiers communicating with the optical source(s); one or more laser diodes communicating with the first amplifier(s); one or more phototransistors; one or more splitters communicating with the laser diode(s), the fiber optical cable(s) and the phototransistor(s); and one or more second amplifiers communicating with the phototransistor(s) and the display(s) for boosting the output of the phototransistor(s) prior to submission to the display(s).

In select embodiments of the present invention, each of the processor(s) and display(s) are integral to a personal computer incorporating a monitor.

In select embodiments of the present invention, the display comprises an oscilloscope.

In select embodiments of the present invention, the ported cables incorporate slots having an exterior width in the range of about 1.0 cm to about 2.5 cm and an opening angle of about 5° to about 20°, said slots being spaced apart on said ported cables about 5 cm to about 30 cm along the length of said ported cables.

In select embodiments of the present invention, the F.O. cable comprises an optical fiber; a micro-bending inducer adjacent the optical fiber and a soft resilient armor covering over the micro-bending inducer, such that the inducer and the covering facilitate the formation of micro-bends in the optical fiber upon impinging by solid media external to the covering.

In select embodiments of the present invention, the TDR incorporates one or more RF pulse-modulated reflectometers. In select embodiments of the present invention, the RF pulse-modulated reflectometer(s) comprise a linear sweep generator for generating an analog signal; a circulator communicating with the linear sweep generator for coupling the analog signals from the RF source to the ported transmission cable and coupling the leakage signal from the ported transmission cable to the RF pulse modulated reflectometer via the ported receive cable and the RF receiver; a mixer communicating with the circulator for combining the received leakage signal(s) with a portion of the transmitted analog signal to yield a first output signal; a low pass filter communicating with the mixer for passing only the low frequency spectra in the first output signal, yielding a second output signal having a frequency spectra in the audio range; a high pass audio filter communicating with the low pass filter for passing only the high frequency spectra of the second output signal, yielding a third output signal having a frequency spectra in the upper end of the audio range; an audio amplifier in operable communication with the high pass audio filter for amplifying the third output signal, yielding a fourth output signal; and a processor communicating with the audio amplifier for comparing the data on features of the received leakage signal with one or more reference signals and displaying results of the comparison, such that employment of the pulse-modulated RF reflectometer enables alerting to hidden anomalies in the structure.

In select embodiments of the present invention, a single control sub-system operates multiple pairs of ported cables and F.O. cables by multiplexing the analog RF signal(s) and the received leakage signals and by multiplexing the transmitted and reflected and refracted optical signals.

In select embodiments of the present invention, a method simultaneously employs complementary techniques to dynamically detect and locate hidden anomalies in structure. The method comprises providing an RF sub-system comprising one or more pairs of transmitter and receiver ported coaxial cables; one or more RF sources communicating with the transmitter ported coaxial cable(s), such that an RF source provides one or more RF analog signals; and providing one or more RF receivers communicating with each of the receiver ported coaxial cable(s), such that each of the RF receivers receives the RF analog signal leaked from ports of the ported transmitter coaxial cable(s) as provided by the receiver ported cable(s): providing an optics sub-system comprising one or more F.O. cables; one or more optical transceivers communicating with the one or more F.O. cables; providing a control sub-system for operating the RF sub-system and the optical sub-system, the control sub-system communicating with each of the RF and the optical sub-systems, the control system comprising: one or more processors, one or more displays communicating with one or more processors; one or more I/O devices communicating with the processor(s) and the display(s); and one or more communications devices communicating with the I/O device(s); installing the pair(s) of ported cables and the F.O. cable(s) entirely within the structure, paralleling the longitudinal axis of the structure; connecting the optical sub-system to the F.O. cables and the control sub-system; connecting the RF sub-system to the ported cables and the control sub-system; operating the RF sub-system and the optical sub-system to obtain, process, display and archive baseline data; and operating the system in accordance with user requirements to detect and locate hidden anomalies by comparing dynamically received data with archived baseline data.

In select embodiments of the present invention, the method employs directional drilling to install the ported cables and the F.O. cable(s).

In select embodiments of the present invention, the method comprises providing a telemetry sub-system communicating with the control sub-system and including with the telemetry sub-system a cellular phone.

In select embodiments of the present invention, the method integrates a TDR system with the RF sub-system.

In select embodiments of the present invention, the method integrates an OTDR system with the optical sub-system.

In select embodiments of the present invention, the method integrates the processor(s) and the display(s) in one or more personal computers, each incorporating a monitor.

In select embodiments of the present invention, the method provides ported cables having integral slots with a width in the range of about 1.0 cm to about 2.5 cm and an opening angle of about 5° to about 20°, the slots being spaced apart on the ported cables about 5 cm to about 30 cm along the length of each of the ported cables.

In select embodiments of the present invention, the method provides F.O. cable(s) incorporating an optical fiber; a micro-bending inducer adjacent the optical fiber(s) and a soft resilient armor covering over the micro-bending inducer, such that the inducer and the covering facilitate the formation of micro-bends in the optical fiber(s) upon impinging of the F.O. cable by solid media external to the covering.

In select embodiments of the present invention, the method provides the TDR as one or more RF pulse-modulated reflectometers.

In select embodiments of the present invention, the method employs a step function with a fast rise time to simulate a pulsed analog RF signal.

In select embodiments of the present invention, the method provides the analog signal as an RF pulse-modulated signal.

In select embodiments of the present invention, the method further provides processing that yields a measure of the time for a known portion of the optical analog signals to travel from the source end to impinging locations along the length of the F.O. cable and the reflection of the optical signal back to the source end.

In select embodiments of the present invention, the method provides processing that employs an algorithm to extract location of the anomaly along the length of the structure.

In select embodiments of the present invention, the method provides for comparing one or more features of the reflected signals to one or more reference signals to yield additional information for decision making.

In select embodiments of the present invention, the method further provides for digitizing the reflected and refracted optical signals and processing them using a Fast Fourier Transform (FFT) algorithm, such that the processing yields a power spectrum from which location and relative amplitude may be identified and displayed on a computer monitor.

Refer to FIG. 1, a simplified diagram and perspective view of an embodiment of the present invention as incorporated in a structure 100 such as a levee. In select embodiments of the present invention, the "basic section" installed in the structure 100 comprises two major sub-systems, a "paired" ported cable portion 101, 102 (see also FIGS. 2A, 2B) and a F.O. cable portion 103 that uses a single F.O. cable 103 for both transmitting and receiving. Preferably, an RF electronics package comprising at least a transmitter 101A and an RF receiver 102A and an opto-electronics package, comprising at least an optical transceiver 103A, a "local" controller 108 in operable communication with both "packages," and a telemetry unit 106 are located immediately outside the structure 100 for easy access for adjustment and maintenance. In addition, a processor, one or more displays, an archiving system and an alarm, are preferably co-located remotely with a decision maker.

In select embodiments of the present invention, an RF transmitter 101A transmits an RF signal through the ported transmitter coaxial cable 101 (hereafter transmitter cable 101) that runs parallel to the long axis, L, of the structure 100, such as within the toe of an earthen levee or dam. An RF receiver 102A is connected to the ported receiver coaxial cable 102 (hereafter receiver cable 102), running parallel to the transmitter cable 101. An F.O. cable 103 may be installed parallel to the ported coaxial cables 101, 102 or may be wrapped in a loose spiral (FIG. 2A) around either of the ported coaxial cables 101, 102 for ease of installation of the F.O. cable 103. For a large structure 100, it may be beneficial to install multiple pairs of ported coaxial cables 101, 102 together with an associated F.O. cable 103 for each pair, the additional installations being parallel to a first installation but at a different depth or at a different separation within the structure, or both at a different depth and a different width to accommodate the shape of the structure 100.

In select embodiments of the present invention, the transmitter cable 101 carries a gated RF signal. The appropriate signal parameters are site dependent since the slot impedance varies as a function of soil parameters. Typical transmitted signal levels range front about 10 dBm to about 40 dBm with a receiving sensitivity over a 500 meter length of about 120 dBm. An RF signal is leaked from ports (slots) 102E (FIG. 2A) of width, w, cut through insulation 102C at an angle, $\phi_0$, and spaced at a distance, $\mu$, along the ported cables 101, 102. The dimensions and spacing of the ports 102E are set to meet a user's requirements. This results in a "leaked signal" being provided along the transmitter cable 101 in a directional pattern 107 (FIGS. 2B and 3) to both intersect the media between the transmitter cable 101 and the receiver cable 102 and provide sufficient signal strength to establish a baseline signal at a "standard" dielectric coefficient of the media, established as measured at installation of the ported coaxial cables 101, 102. Thus the slots (ports) 102E in the ported coaxial cables 101, 102 are oriented to face like slots 102E in the other cable of a cable pair and provide optimum "gain" as well as "irradiation" of the media for the leaked signal in the direction of the receiving cable 102. For select embodiments of the present invention the value of $\phi_0$ (FIG. 2B) is between about 5° and about 20° (FIG. 2B) and preferably about 7.5°.

As a leaked RF signal from one of the slots 102E propagates through an area in the structure 100 near which an anomaly 105 occurs, such as water seepage in a levee or dam, the signal received by the receiver cable 102 changes. That is, coupling between the ported coaxial cables 101, 102 changes due to change in the dielectric coefficient of the media that may be due to a change in moisture content. The returned signal represents the degree of coupling along the cable and depends upon the dielectric. $\in_4$ (FIG. 2B), of the media, typically an at least partially silty soil of a levee or dam 100, in which the wave propagates.

The time of travel of the impressed RF signal through the transmitter cable 101 to the anomaly 105 plus the time of travel back through the receiver cable 102 from the location of the anomaly 105 determines the location of the anomaly 105 along the structure 100. Further, changes in time and frequency domain characteristics of the received signal compared to the transmitted signal may be used to determine physical characteristics of the anomaly 105. The location and severity of the anomalies 105 are identified to a decision maker at the control sub-system 111 (FIG. 11).

Specifically, for an earthen structure 100, characteristics of an RF signature vary with moisture content of the material between the two ported coaxial cables 101, 102. Further, displacement of soil is indicated by change in signal characteristics on the F.O. cable 103. Either displacement of material or vibrations transmitted through the structure 100 may be detected in received optical signals and are indicated by changes in the distance traveled by the reflections of the impressed light signal, preferably white light pulses.

In select embodiments of the present invention, sensitivity may be adjusted by adjusting the power output of the RF transmitter 101A. Further, a "basic" system may be extended to considerable length by incorporating amplifiers 901 (FIG. 9) in both the transmitter 101 and the receiver 102 cables. In remote areas, multiple systems may be linked to a remote processor 109 (FIG. 11) and display/alarm 110 (FIG. 11) by a communications network such as indicated by the telemetry unit 106. Further, select embodiments of the present invention envision a system comprising multiple layers, i.e., ported cable 101, 102 and F.O. cable 103 "sets" (FIG. 9) installed at multiple depths in the structure 100, especially in those structures 100 of considerable height.

Figure 11:
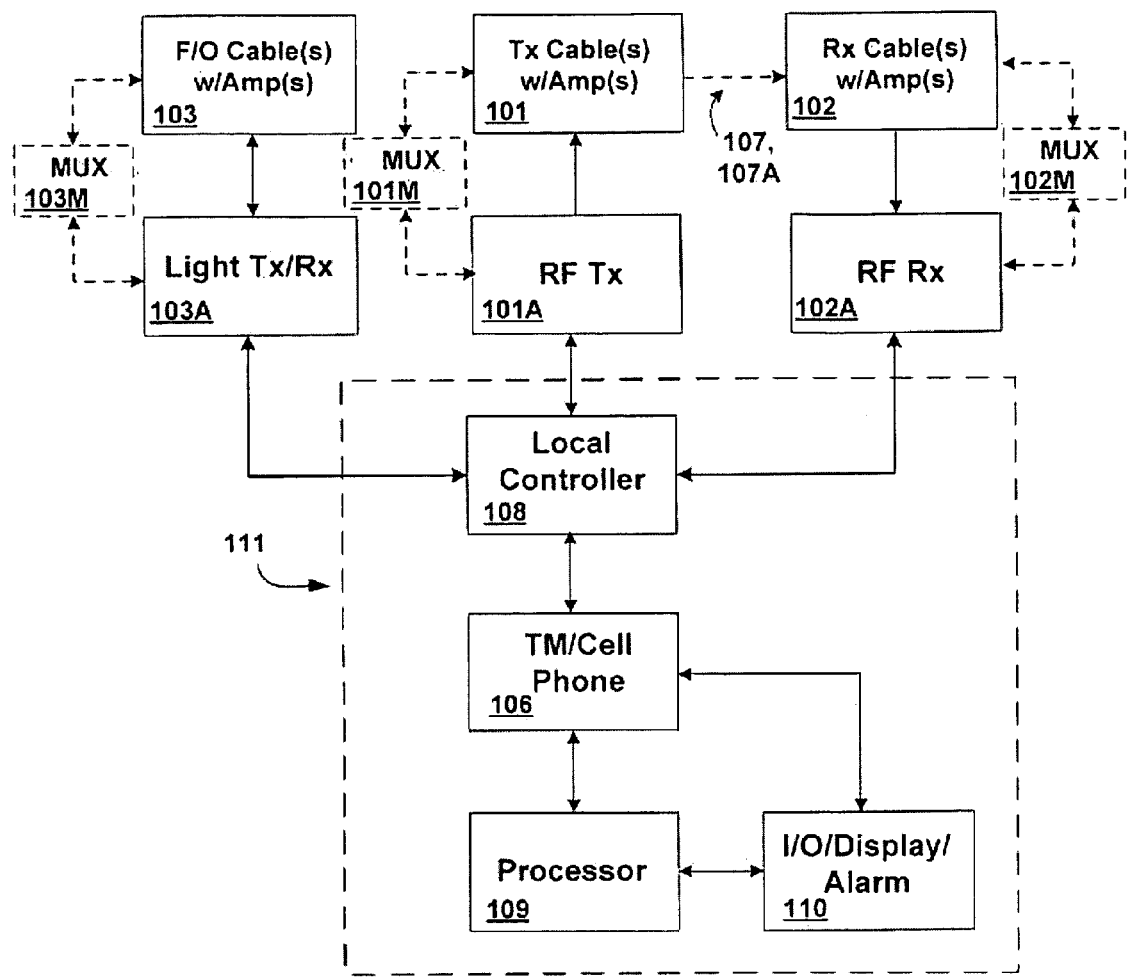
FIG. 11 is a block diagram of major elements comprising an embodiment of the present invention.

Refer to FIG. 11, a simplified block diagram describing basic elements used with select embodiments of the present invention. Three cables 101, 102, 103 are installed in an earthen structure 100, such as a levee or dam. If the earthen structure 100 is of considerable length the cables will have associated amplifiers installed along their length at appropriate points. One or more RF transmitters 101A will feed the transmitter cable(s) 101 and one or more RF receivers 102A will receive both the "baseline" response 107 and any responses 107A indicating a possible anomaly 105. The F.O. cable 103 is connected to an optical transceiver 103A that both transmits light pulses and receives the reflected light from the F.O. cable 103. In select embodiments of the present invention all the cables 101, 102, 103 and associated transmitters 101A, receivers 102A and transceivers 103A are controlled by a local controller 108 that also inputs via a telemetry unit 106 or cellular phone (not shown separately) to a remote processor 109 that is accessed by a multi-functional I/O, display and alarm device 110 such as may be incorporated in a personal computer (not shown separately). As shown in FIG. 11, the multi-functional device 110 has communications to both the processor 19 and the local controller 108 via the telemetry unit 106 (or alternatively a cellular phone). Also shown in FIG. 11 is an alternate configuration employing multiplexers 101M, 102M, 103M for feeding multiple RF ported cables 101, 102 and F.O. cables 103 in large structures 100 requiring the multiple cables 101, 102, 103.

In select embodiments of the present invention, an RF gated transmitter 101A (see also FIGS. 8 and 11) drives a ported transmission cable 101 with an RF signal, f(t), where $$f(t)=A\cos(\omega t)*B(t) \quad (1)$$

Figure 2A:
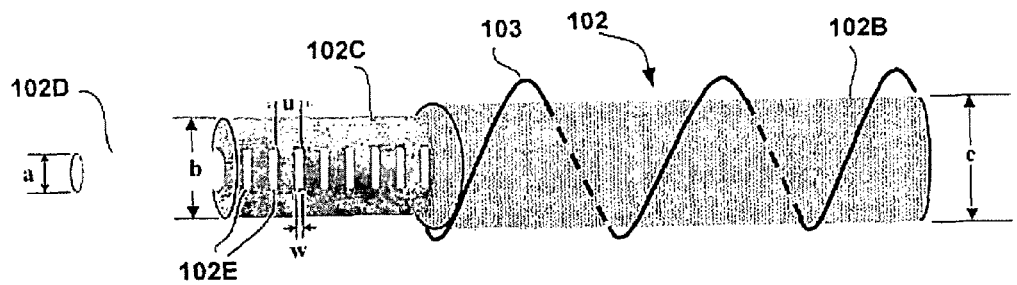
FIG. 2A is a cut-a-way profile drawing of a ported cable that may be used in select embodiments of the present invention.
Figure 2B:
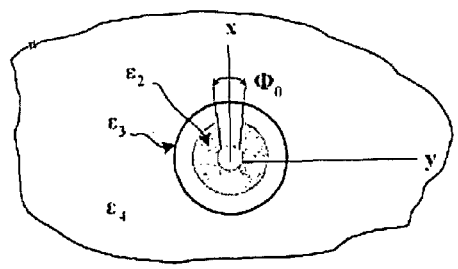
FIG. 2B is a cross sectional end view of the ported cable of FIG. 2A.
Figure 3:
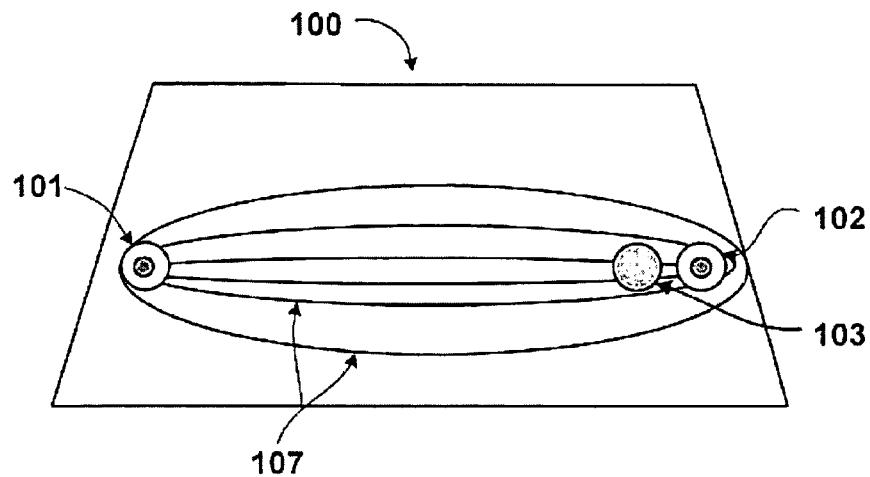
FIG. 3 is a cross-sectional view of the levee of FIG. 1 indicating resultant electromagnetic field lines that are possible.

A portion of the signal is referenced back 803 (FIG. 8) to a receiver 102A to compare to the received signal. The coefficient, A, represents the power level at which the signal is transmitted and $\omega t$ represents frequency, while B(t) represents the gate period applied, allowing adjustment for maximum length of a levee 100, for example. In select embodiments of the present invention, the frequency is in the range of about 20 MHz to about 100 MHz. Parallel and adjacent to the transmitter cable 101, at some distance depending on the type of soil, cable material and the power level, is a receiving cable 102, a ported cable similar to the transmitting cable 101. As the gated RF signal propagates along the ported transmitter cable 101, a portion of it is coupled to the receiving cable 102 via the slotted ports 102E (FIG. 2A). The amount of coupling depends upon the type of soil and the amount of moisture within the soil, both of which are factors contributing to the soil's dielectric constant. $\in_4$ (FIG. 2B). A baseline coupling value, along the length of the cables 101, 102 is established once the cables 101, 102 are installed.

To establish "guidelines" for use of select embodiments of the present invention in earthen structures requires a system operator to gather information on the general characteristics of the soils used in constructing the specific earthen structure 100 to be monitored. The soil types along the path of the buried cable define the range of expected changes in dielectric properties due to changes in moisture. Therefore as the cables are emplaced, the soil is characterized by collecting soil samples along the path of the installed cables, recording location and depth by soil type, e.g., silty clay, and characteristic, e.g., moisture content at installation. The use of resistivity, temperature and moisture probes as well as select drilling and historical data provides additional calibration of the cable, in particular response to variations in moisture. The clays will have a larger range of attenuation than the sands, therefore measurements of soil moisture changes during a dry period and wet period will allow for "seasonal" changes in calibration. For example, interpolation of the moisture profile between stations may be accomplished using an appropriate geostatistical technique to derive a continuous profile of moisture changes for the entire length of a buried cable. An attenuation of the signal may be then cross-correlated to changes in moisture along the length of the cable. Also, external data, such as that available from a weather station, e.g., historical rain fall patterns, humidity variation and wind speed histograms may be factored into the estimate.

Figure 4:
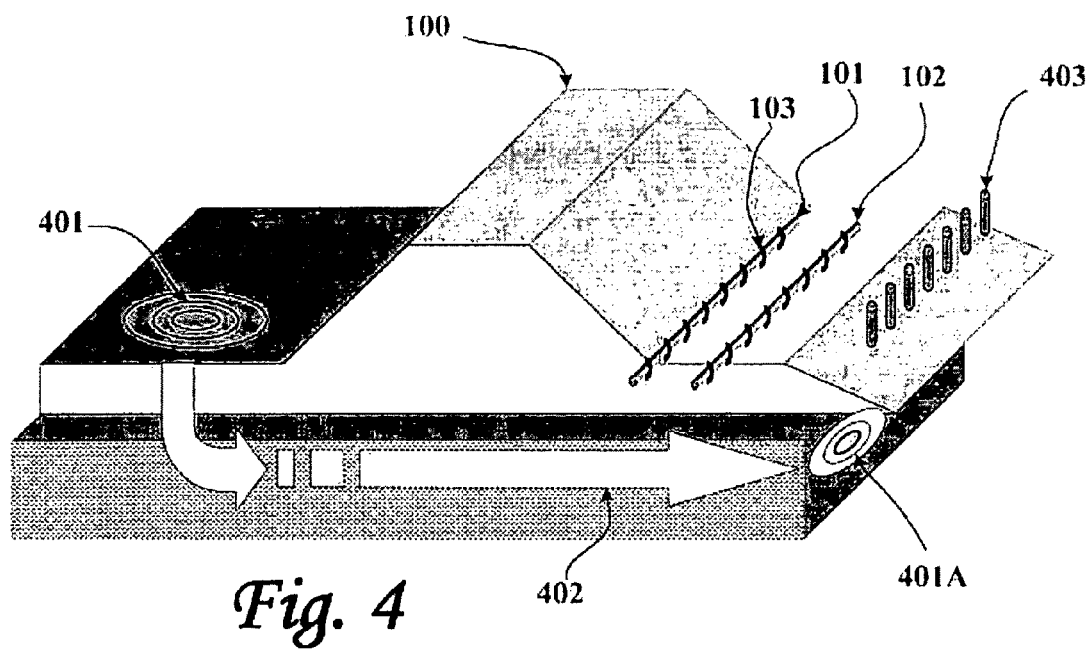
FIG. 4 depicts a structure and detected abnormal sand boil.

Refer to FIG. 4, in which resistivity, moisture and temperature measurements are being made by probes 403 inserted in conjunction with installation of "wrapped" ported cables 101, 102. FIG. 4 also depicts how an anomaly such as a sand boil 401 is detected as an anomaly 401A introduced via resultant seepage 402 through the earthen structure 100. Although this may be detected by the probes 403 initially, continuous monitoring is optimized via the simple installation of the ported coaxial cables 101, 102 and one or more F.O. cables 103.

In select embodiments of the present invention, the received RF signal is given by $$f(t)'=A' \cos(wt+1_n)*B'(t) \qquad (2)$$

After removing the baseline values, the received signal is compared to the reference signal 803 wherein the value of coupling is determined at each point along the length of the cables 101, 102. In addition to the value of coupling, the approximate position of the coupling is determined along the length of the cables 101, 102, e.g., at $R_c$ and $R_d$, by scaling the time of travel from B(t) until B'(t).

Figure 9:
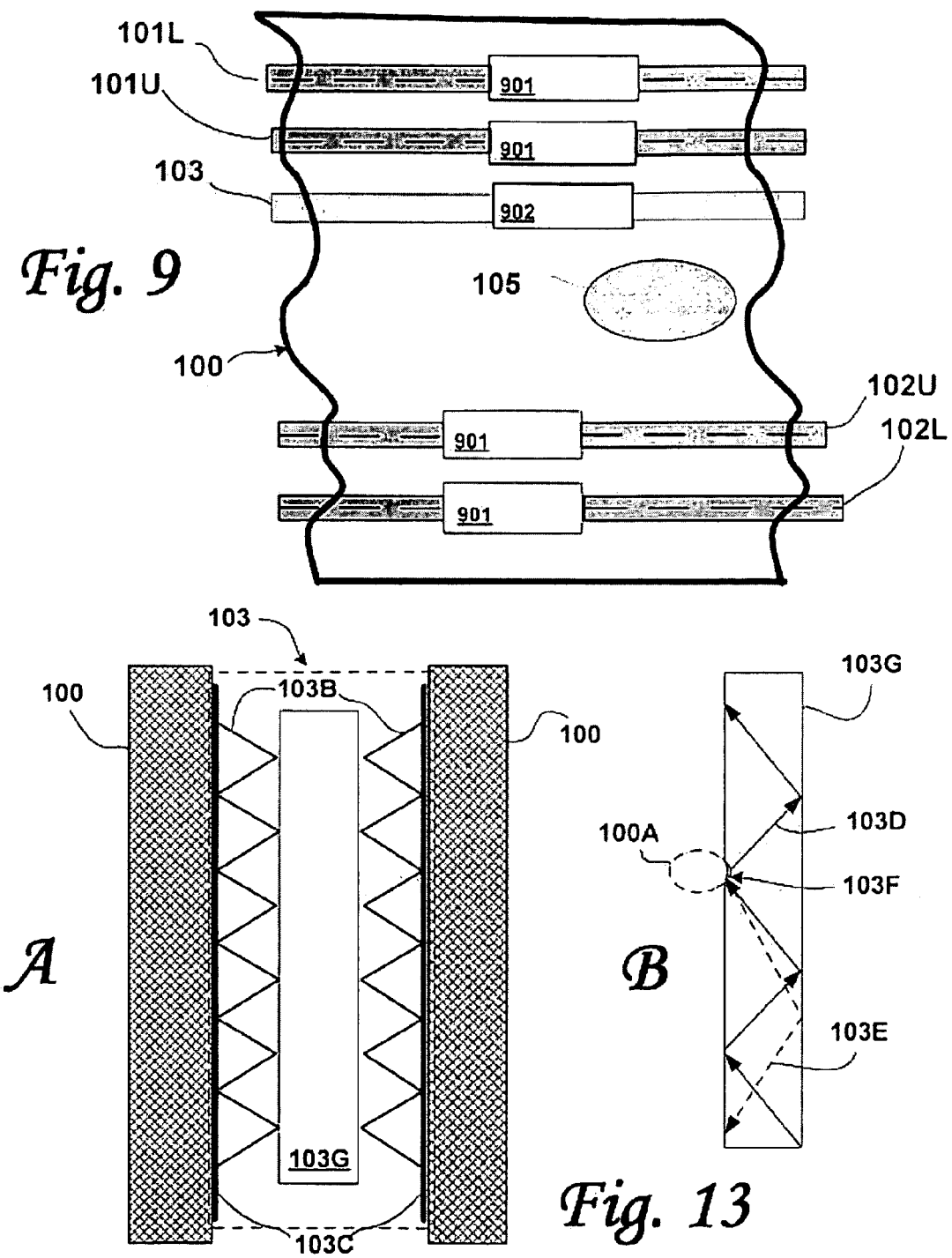
FIG. 9 is a top view of a section of levee in which multiple transmit/receive pairs of cables and optical cables have been installed at varying depths in a levee as may be further enhanced for operation over a long distance inside the levee.

Refer to FIG. 9, showing a section of the structure 100 of FIG. 1 in a top view incorporating ported cables 101L, 101U, 102L and 102U and F.O. cable 103. Pairs of ported cables at a lower elevation 101L, 102L and at an upper elevation 101U, 102U within the structure 100 are shown. If the structure 100, e.g., an earthen levee or dam, is sufficiently long such that the ported cables 101L, 102L, 101U, 102U, or F.O. cables 103 would be extended beyond their range of operation, the range may be extended by utilizing amplifiers 901, 902. Of course, the optical amplifiers 902 are bidirectional and the F.O. cables 103 are located optimally to detect movement (displacement) within the structure 100.

Figure 5:
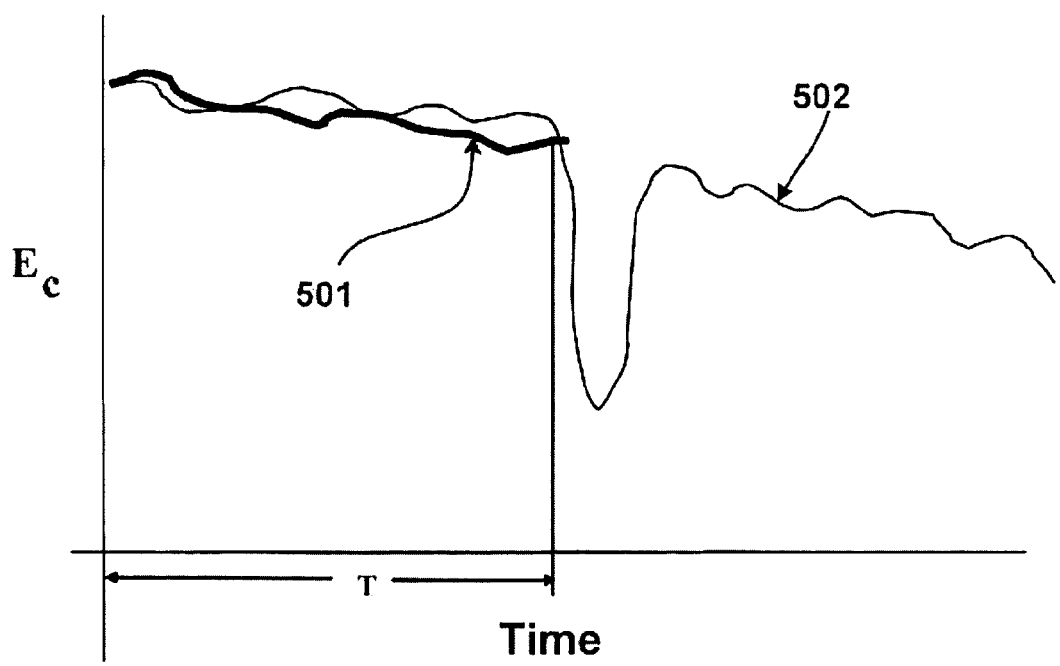
FIG. 5 depicts a received signal that indicates a change in moisture at a specific location in a structure.
Figure 8:
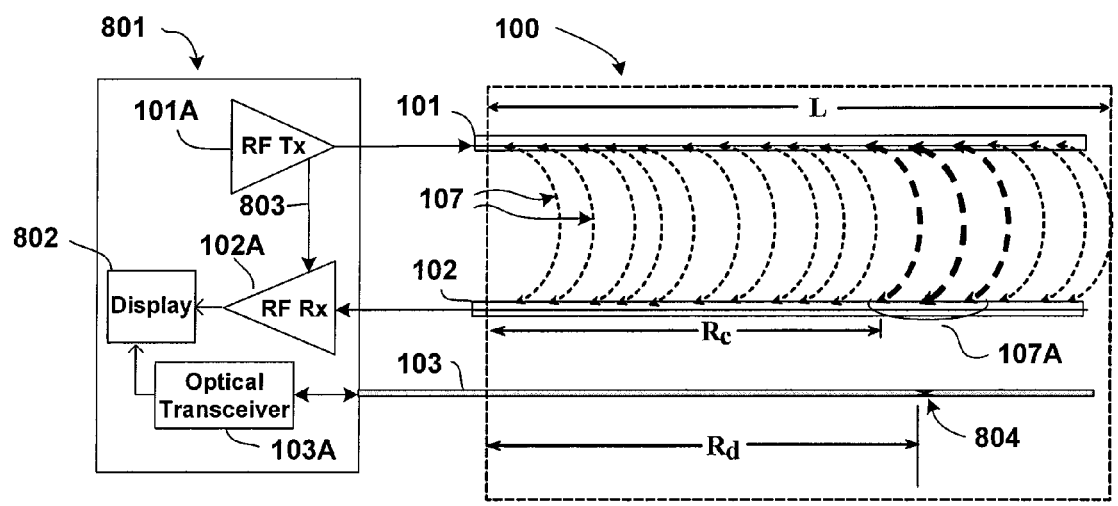
FIG. 8 is a simplified block diagram of a system representing an embodiment of the present invention as related to the installation of its cables in a levee.

Refer to FIG. 5 for a comparison of the baseline response 501 as a voltage, $E_c$, over time to an actual response 502, indicating an anomaly (discontinuity) beginning at time, T. The distance down the cable (levee) to where the discontinuity occurs is shown in FIG. 8 as $R_c$ and is related to time propagation time of the RF signal down the ported transmission cable 101. The dielectric of the media, $\in_4$ the media generally being soil, is determined in the main by the amount of moisture and type of material and must be established as a baseline at least upon first installation of the cables 101, 102, 103. Of course, as the material and its moisture content varies along the length of the structure the dielectric constant, $\in_4$, must be determined for each change in the material and its "baseline" moisture content. Changes in dielectric constant must be taken into account for the RF signal and any processing algorithms adjusted to account for each different "baseline" dielectric constant along the length of the ported cables 101, 102.

Figure 6:
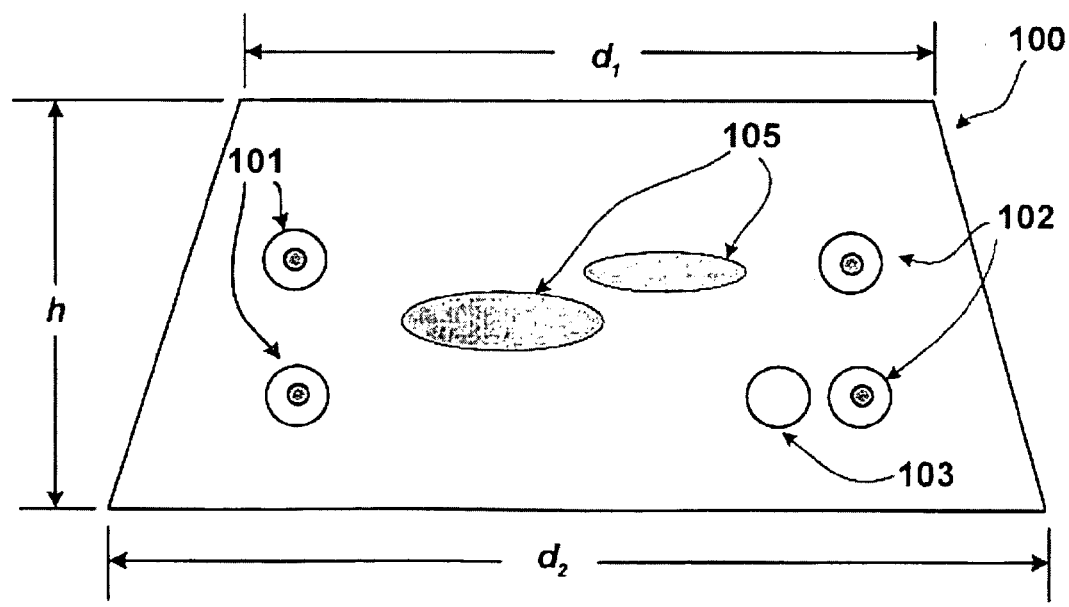
FIG. 6 is a cross-section through 6-6 of the levee of FIG. 1 showing multiple ported cables and a fiber optic (F.O.) cable.

An area of high continuity 105 (FIGS. 1, 6, 8) compared to the baseline indicates a potential problem, e.g., a seepage path in a levee. Within this area 105 the "leakage signal" from the ports 102B (FIG. 2A) propagates across as a weaker signal as shown in FIG. 1 at 107A, being attenuated by the increase in the dialectic constant, $\in_4$, caused by the increased moisture. In select embodiments of the present invention, the RF receiver 102A forwards the received signal, preferably via a telemetry unit 106 (FIG. 1) that may also communicate via a cellular phone, to a processor 109 that analyzes it. The processor is in operable communication with a display/alarm 110 (FIG. 11) and the telemetry units 106, although a "local" display 802 (FIG. 8) may also display processed data as appropriate. Either of the displays 110, 802 may output a warning that is analog, digital, visual, aural, or any combination thereof. Further, any local or remote manner of providing an alert about hidden anomalies may be used. For example, a CRT or other display interface for a human operator may be used for visual alerting. An audible signal may also be provided, or both a visual an audible signal may be provided as well as an analog or digital signal to an automated system for recording and further processing to prepare an appropriate response. Remote notification may be by radio signal (e.g., telemetry or cellular phone) or hard-wired network, either dedicated or public.

A subsurface anomaly 105 may also present via the F.O. cable 103 as a seismic signal, i.e., physical displacement over time. In select embodiments of the present invention, this is established by using OTDR principles for measuring changes in arrival time of a pulsed light signal as compared to a baseline.

Figure 7:
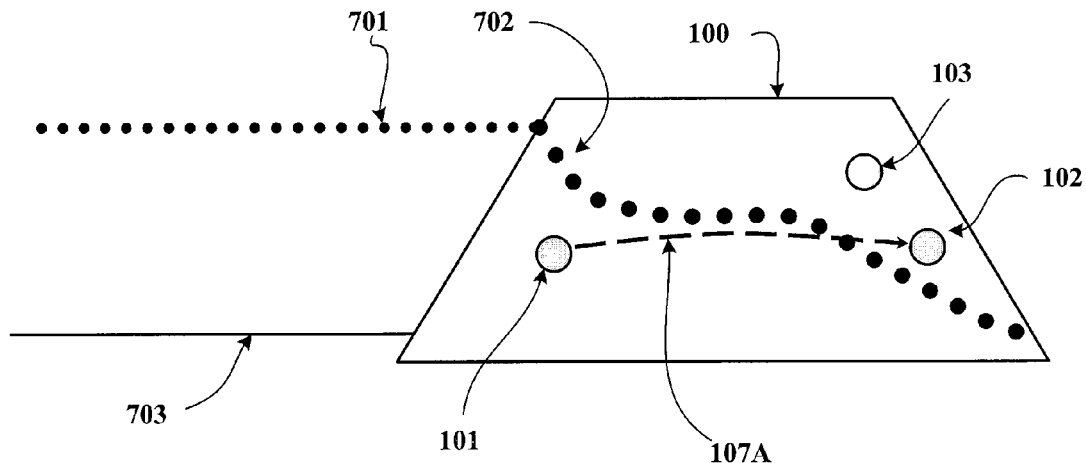
FIG. 7 is a simplified line drawing of an end view of a levee experiencing seepage that shows a minimal underground installation of the cables of an embodiment of the present invention.

Refer to FIG. 7, an end view through a cross section of a levee such as at 6-6 of FIG. 1 also depicting the water level 701 and bottom 703 of a water impoundment. For illustration simplicity, only one ported transmitter cable 101 and one ported receiver cable 102 are shown installed. For select embodiments of the present invention, FIG. 7 shows how the ported cables 101, 102 may be "buried" (emplaced) on each side of a typical earthen levee 100 approximately at the same depth within the structure and parallel one to the other. The F.O. cable 103 is shown running parallel to the receiver cable 102 although it may be placed nearer the transmitter cable 101 in alternative embodiments. FIG. 7 also shows a representation of electric field line 107A inducing an attenuated received signal in the receiver cable 102. A sub-surface anomaly, in FIG. 7 indicated by the seepage line 702 and in FIG. 1 by the shaded area 105, such as increased moisture, decrement of soil, and the like, can be located by simple measurement of the change in propagation time due to the change in the dielectric constant, $\in_4$, of the surrounding media. Alternatively, when it is helpful to correct for echoes and like phenomena that introduce errors, the transmitted signal may incorporate a time-varying characteristic, in turn generating a time-varying characteristic in the received signal, $R_c$ (FIG. 8). The change in the received signal, $R_c$, caused by a sub-surface anomaly 105, 702 as indicated in the time varying characteristic establishes the location of the subsurface anomaly 105, 702 using the well-known TDR principle. The amplitude of the received signal, $R_c$, may also provide a measure of the severity of the anomaly 105, 702.

Processing of Collected RF Data

Select embodiments of the present invention may be implemented in at least two manners: using conventional time domain reflectometry (TDR) or using a pulse-modulated technique. Inherent advantages of select embodiments of the present invention include: robust construction; minimally complex user interface; no moving parts during operation;

low maintenance as compared to conventional methods; straightforward installation; and ability to automatically reset.

In select embodiments of the present invention an electronics package via a local controller 108 (FIGS. 1 and 11) is directly connected to a pair of ported coaxial cables 101, 102 to function as a Time Domain Reflectometer (TDR). The principle of TDR is widely known, described in the technical literature, and applied to numerous measurement and testing applications. TDR operates by generating an electro-magnetic pulse (or a fast rise time step) and coupling it to a transmission line. That pulse propagates down the transmission line at a fixed and calculable velocity, a function of the speed of light and the electrical and physical characteristics of the transmission line. The pulse will propagate down the transmission line until the end of the line is reached, and then will be reflected back towards the source. The time, t, that it takes for the pulse to propagate down and back the length of the transmission line is called the "round trip travel time" and is calculated as:

$$t = \frac{2L}{v}. \quad (3)$$

where:
L=length of the ported receiver cable (m)
v=velocity of propagation (m/s)

The propagation velocity is:

$$v = \frac{c}{\varepsilon^{\frac{1}{2}}} = \frac{c}{n} \quad (4)$$

where:
c=velocity of light in free space ($3 \times 10^8$ m/s)
$\varepsilon$=the relative dielectric constant of the media surrounding the ported cables
n=index of refraction of the media surrounding the ported cables Changes in the dielectric media in the volume immediately surrounding the ported cables cause a change in the round trip travel time. Freshwater has a dielectric coefficient, $\varepsilon_w$, of 88; dry sedimentary materials (e.g., soil, gravel and stone) have an $\varepsilon_s$ in the range of 5 to 8. Wet soil has a dielectric coefficient that is a mixture of those of water and dry soil. The dielectric coefficient, $\varepsilon_{s+w}$, of this mixture will vary depending upon the local soil constituency, but in all cases the bulk dielectric (bulk index of refraction) of the mixture will be less than that of liquid water alone and significantly greater than that of the dry soil. Some soils, particularly clay-based soils, are extremely lossy. This lossy behavior of the soil is exhibited by a severe attenuation of an electromagnetic pulse as it propagates across the soil via a leaky transmission line (ported cable) surrounded by such materials.

At any boundary at the ports 102E along the ported cables 101, 102 (e.g., water/soil, moist soil/dry soil) a dielectric discontinuity exists. As a pulse leaking from a transmission cable 101 to a receiver cable 102 encounters these boundary conditions, a portion of leaked energy is sent back to a receiver 102A from the boundary and a portion of the energy continues to propagate through the receive cable 102 Measuring the time of flight of the pulse and knowing the dielectric medium through which the pulse is normally traveling permits calculation of the physical distance from the receiver 102A to each of the dielectric interface boundaries encountered. Further, any change in amplitude of the received pulse indicates a change in the dielectric coefficient and the presence of an anomaly 105. Judicious selection of the slot size and separation of slots 102E in the ported coaxial cables 101, 102 to meet a user's requirements enables determination of both the severity and location of hidden anomalies 105 within the earthen structure 100.

RF pulse-modulated techniques are well known in radar system applications. Instead of launching energy from an antenna into free space, as would be done in a radar application, energy is coupled to a ported transmission cable 101. In a RF pulse-modulated system, a signal of constant amplitude whose frequency changes linearly with time is transmitted. While for the vast majority of applications the linear frequency-time relationship is employed, conceivably there are also applications in which a sinusoidal, exponential, logarithmic, or other frequency-time relationship may be useful. A RF pulse-modulated signal may be produced by n voltage controlled oscillator (VCO) driven by a linear ramp generator. The signal propagates down the ported transmission cable 101 and is effectively terminated from the far end and "leaked" at intermediate discontinuities represented at the ports (slots) 102E, returning to the receiver 102A via the receive cable 102, delayed by the round-trip propagation time, $2t_p$. This returning attenuated signal is mixed with a sample of the VCO output that is fed directly to the mixer with a minimal, but known, delay. The mixing process-produces sum. $\Delta f$, and difference. $\Delta f$, frequency spectra. Low pass filtering is applied to retain only $\Delta f$. Within $\Delta f$, one component, $F_D$, is proportional to the distance, D, to the receive slot 102E of the parallel receive cable 102 and can be determined using spectral analysis techniques. For a transmission line surrounded by a homogenous dielectric medium with a refractive index n, D is found from:

$$D(m) = \frac{(F_D)(t_{mp})c}{2(BW)(n)} \quad (5)$$

where
$F_D$=difference frequency due to transmission line impedance discontinuity reflection (Hz)
$t_{swp}$=RF pulse-modulated sweep time (s)
c=velocity of light in a vacuum (m/s)
BW=RF pulse-modulated swept bandwidth (Hz)

The difference frequency spectra usually lie in the audio range. The spectra have a similar appearance to a time domain reflectometry (TDR) scan and can be calibrated as such with distance, D, related to the round-trip travel time, t, by:

$$t = \frac{2Dn}{c} \quad (6)$$

In select embodiments of the present invention, a typical implementation of an RF pulse-modulated transmission line sensor system may comprise several electronic components (not separately shown). A sweep generator comprising a linear ramp generator and voltage controlled oscillator (VCO) may be used to supply a signal. The linear ramp generator is used to drive an RF voltage controlled oscillator (VCO) with sufficient swept bandwidth (typically about 100 MHz to about 1000 MHz of bandwidth) to provide the required resolution. The output of the sweep generator is coupled to the transmission cable 101 through a circulator or similar device, e.g., a "T", "Magic T", power splitter, or the like, that transfers the signal from the VCO directly to the transmission line. The swept signal propagates down the transmission cable 101, leaking from the slots 102E, is received by the receive cable 102, reaches the distal end of both ported cables 101, 102 and is effectively terminated, only the portions of the signal leaked at each slot 102E returned to the circulator or equivalent device. At the circulator, the returned signal is routed to a mixer diode. There it is mixed with a separate leakage signal that has propagated across the short path between the VCO and the mixer. The resulting output of the mixer consists of a summed high frequency signal, Σf, and a low frequency, audio-range difference signal, Δf. An RF low-pass filter (LPF) passes Δf and attenuates Σf to a level making it inconsequential. Next, the resultant "passed" signal is filtered through an audio high-pass filter (HPF) to remove DC and low-frequency audio components associated with any near-end terminal reflections. An audio amplifier may be used to amplify the signal as needed for subsequent signal processing. This signal may be processed directly, analyzed, and stored or displayed. Alternatively, this signal may be transmitted to a remote location over twisted pair, coaxial cable, radio, cellular phone or other form of telemetry, where it may be processed, analyzed, displayed, further distributed and archived.

There are several methods by which the resulting, audio signal may be processed. It may be viewed directly on an audio-frequency spectrum analyzer or the like wherein spectral peaks indicate interface boundaries. Using a personal computer or the like, it may be digitized and processed by a Fast Fourier Transform (FFT) algorithm, resulting in a power spectrum in which spectral peaks indicate interface boundaries. Another alternative employs a bank of tuned, narrow-band, audio band-pass filters (BPF), closely spaced in center frequency, each interfaced to a light emitting diode (LED) wherein progression of illuminated LEDs indicates change in the dielectric constant of the media.

To minimize the energy reflected by the interface at the slots 102E of the ported cables 101, 102 with the boundary at the slots 102E, thus permitting a greater portion of the energy to propagate through the surrounding media, the ported cables 101, 102 are impedance matched to the surrounding "baseline" media. Impedance matching may be accomplished in two ways: by using an impedance transformer or, preferably, by designing the physical dimensions of the slots 102E to ensure an impedance match with a typical soil in the earthen structure 100. To simplify fabrication, the latter method is preferred but may not be practical given large variance in soil types used in earthen structures 100. The characteristic impedance, $Z_0$, of a transmission cable 101 is calculated by:

$$Z_0 = \frac{120}{\sqrt{\varepsilon}} \cosh^{-1}\left(\frac{1}{2a}\right) \quad (7)$$

where α=is the radius of the conductor.

In select embodiments of the present invention, the transmission cable 101 may be designed to have a $Z_o=25\Omega$ when immersed in a representative silly or clay soil. As an example of the effects of an impedance mismatch, a 50Ω ported coaxial cable provides about 3.5 dB of loss in a silly soil of a given moisture content. It is, however, able to produce a necessary reference signal delineating the ported cable slot 102E to media interface. In this implementation, impedance matching is important for the section of the ported cables 101, 102 that are un-insulated. i.e., surrounded by typical silty soil alone, such as the slots 102E. This impedance changes as the dielectric medium (e.g., water or water/soil mix) surrounding the ported cables 101, 102 changes; however, this difference does not significantly affect the ability of the system to clearly delineate the interface boundaries necessary to identify changes in the dielectric medium and locations thereof.

The dimensions of the ported cables 101, 102 may be varied, depending on the application; however, in typical applications, two parallel lengths of 14 gauge ported coaxial cable, spaced about 3 m (about 10 ft) center-to-center are suitable for nominally "dry" silty soil typically used for earthen structures 100. In select embodiments of the present invention, near (exposed) ends of the ported cables 101, 102 are connected to a system RF transmitter and RF receiver, respectively. At the distal end of each ported cable 101, 102 there may be incorporated a terminator (not separately shown).

In select embodiments of the present invention, following installation, an initial reference reading is made and the responses and the round trip travel times for the signal propagating along the ported transmission cable 101 and back, along the ported receiver cable 102 are calculated and stored, preferably in an associated computer (not separately shown). Subsequently, "monitoring" signal responses and round-trip propagation times are acquired, preferably automatically, and signal levels and distances calculated and compared with reference data. In select embodiments of the present invention, a real-lime computer algorithm may be used to compare the reference data with subsequent measurements, trigger an alarm when a significant change is observed in the signal response or a threshold difference in round trip travel time is reached. In select embodiments of the present invention, an automatic, electronic multiplexer may be associated with the control system to monitor an "array" consisting of sets of ported cables 101, 102 and F.O. cables 103 installed within an earthen structure 100.

Processing of Collected Optical Data

An optical TDR-based (OTDR) scour probe that relies on "micro-bending" in an optical fiber is described in U.S. Pat. No. 6,526,189, *Scour Sensor Assembly*, to Yankielun, Feb. 25, 2003, incorporated herein by reference. Micro-bending is caused by changes in the impinging pressure of surrounding material on a specially configured F.O. cable 103 (FIG. 13) to indicate the extent of movement of the F.O. cable 103. Note that no change in the dielectric constant, $\in_4$, of the surrounding material is required for this measurement, thus if the F.O. cable moves as a result of movement (such as subsidence) of material that is at a distance from the material immediately surrounding the F.O. cable, the micro-bending indicates an anomaly 105 within the earthen structure 100 in which the F.O. cable 103 is installed. That is, the anomaly 105 does not have to have its source immediately adjacent the installed F.O. cable 103. The F.O. cable 103 complements the paired ported coaxial cables 101, 102 in this respect since if there is no movement in the soil but there is a change in dielectric constant due to seepage, the ported coaxial cables 101, 102 are able to quickly detect it.

In select embodiments of the present invention, optical time domain reflectometry (OTDR) may be employed. OTDR functions similarly to electromagnetic FDR employing RF signal sources. The main difference between electromagnetic TDR and OTDR is that OTDR relies on photonic energy and an optical waveguide, while FDR relies on electromagnetic energy and a metallic transmission line.

Refer to FIG. 13 depicting a cross section, taken longitudinally, of a specialized F.O. cable 103 that may be used in select embodiments of the present invention. A micro-bend inducer 103B surrounds the optical fiber 103G and in turn is shielded by a soft pliable armor covering 103C. In select embodiments of the present invention, the micro-bend inducer 103B is an elongated tube providing width-wise ridges spaced along its length. In select embodiments of the present invention, the armoring 103C is a soft plastic material. Soil impinging against the soft armoring 103C causes the soft armoring 103C to extend inwardly which, in turn, applies pressure on the micro-bend inducer 103B, causing one or more of the ridges of the micro-bend inducer 103B to engage the optical fiber 103G, creating a micro-bend 103F.

One advantage of a sensor based on an appropriately configured F.O. cable 103 is that it is impervious to the effects of water conductivity. In an OTDR system, a pulse may be generated by a laser or light-emitting diode, or the like, and transmitted by a P.O. cable 103 coupled thereto. The pulse propagates along the F.O. cable 103 at a constant velocity that may be related to the speed of light in a vacuum and the index of refraction of the optical fiber 103G. If there are any irregularities 103F along the F.O. cable 103, in particular those resulting in impinging on the optical fiber 103G itself, as would be caused by a break, sharp bend, external pressure, of other such disturbance, a portion of the pulse's energy is reflected back from the irregularity 103F toward the optical transceiver 103A.

Further, as discussed initially, "point pressure" on the F.O. cable 103 creates "microbends" 103F that also cause back scatter of photonic energy within the optical fiber 103G towards the transceiver 103A, as indicated by the dashed arrows 103E. The time that is required for the light pulse to propagate from the transceiver 103A and back from the irregularity 103F can be determined in a manner similar to that used for an electromagnetic TDR system. However, OTDR is based on the index of refraction of the optical fiber 103G itself and not the dielectric constant, $\in_4$, of the material surrounding the F.O. cable 103. Thus, OTDR is especially useful as an alternative or "complement" to a metallic TDR system, permitting continuous monitoring without regard to the "lossiness" of the media in which the F.O. cable 103 is embedded.

Thus, an optically-based system may detect micro-bending along the F.O. cable 103 due to localized changes in impingement and movement of surrounding granular materials, such as soil. Micro-bending 103F of the F.O. cable 103 at installation, is determined and archived as a baseline since the F.O. cable 103 itself will be enclosed within the soil of the structure 100 and the freely suspended response, as represented by the solid arrows 103D, will be non-applicable. This "baselining," such as detection and archiving of the position of a stone 100A impinging on the F.O. cable 103 as installed, permits ready detection of micro-bending changes encountered after installation that may be related to recently introduced anomalies 105 in the earthen structure 100. Having an awareness of movement beneath the surface, appropriate action may then be recommended on a timely basis.

In select embodiments of the present invention, the F.O. cable 103 may be spirally wound around either of the ported cables 101, 102 (FIGS. 2A, 4) or separately installed parallel to the ported cables 101, 102 (FIGS. 1, 6-9). In select embodiments of the present invention, the optical fiber 103G may be encased in appropriate flexible armoring 103C (FIG. 13), with or without a micro-bending inducer 103B, the flexibility itself permitting development of the micro-bends 103F in the optical fiber 103G. Thus, the location of the interface, or boundary change region at which micro-bending 103F occurs along the F.O. cable 103 will be apparent.

Figure 14:
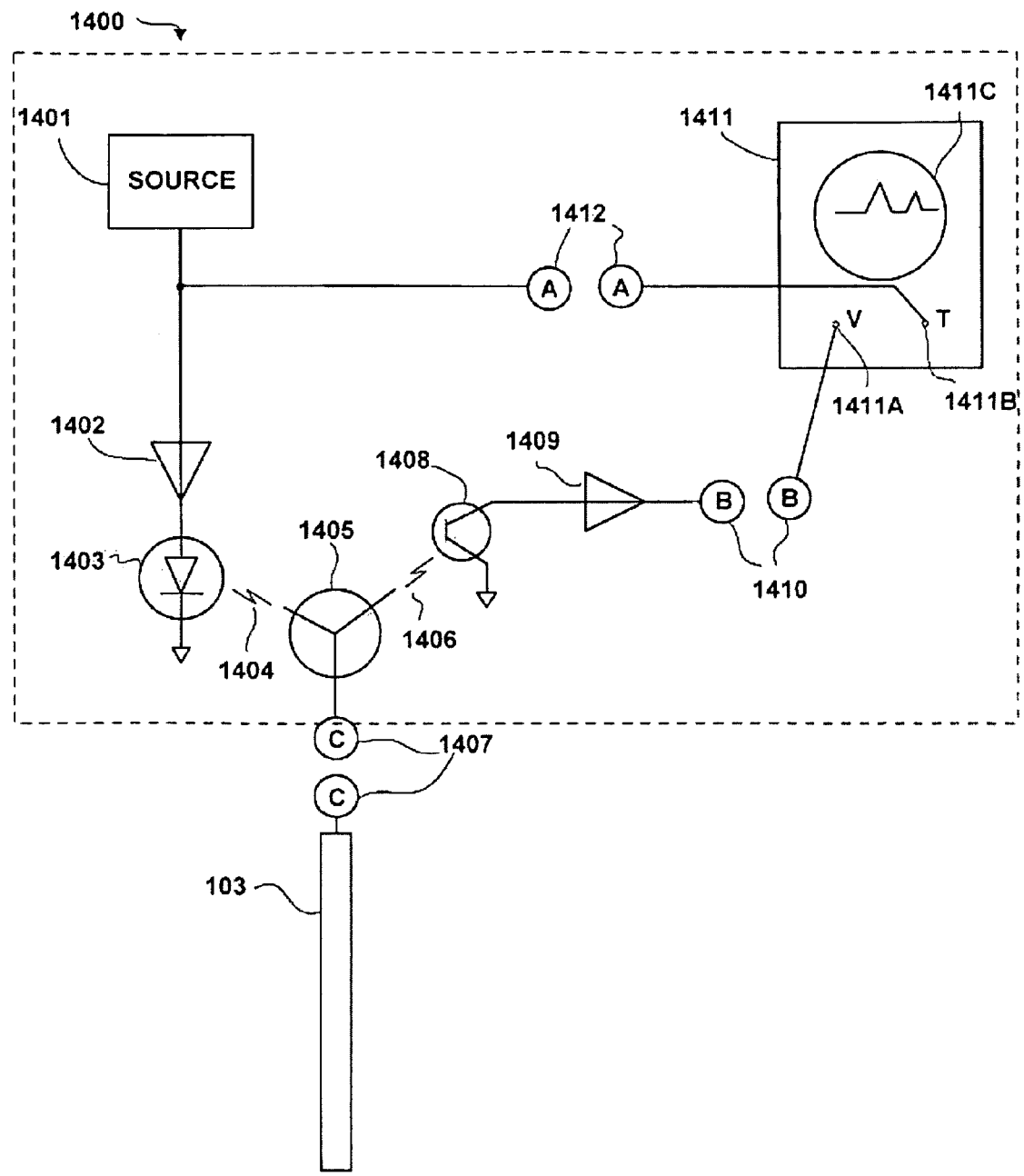
FIG. 14 is a schematic for an opto-electronics package that may be used with select embodiments of the present invention.

Refer to FIG. 14, a schematic of an opto-electronics package implementing OTDR for use with select embodiments of the present invention. At least part of the package may be installed at the entrance of the F.O. cable 103 to the earthen structure 100. By monitoring the change in distance (travel time) and correlating the amplitude of returned energy, anomalous activity within the earthen structure 100 may be tracked continuously.

In select embodiments of the present invention, a train of photonic pulses, preferably having a low duty cycle relative to the pulse width, are generated by a source 1401 such as a pulse generator or the like. In select embodiments of the present invention, the signal is provided by a cable as indicated at 1412 where A-A is a cable connector, to a trigger input, T 1411B, of an oscilloscope 1411. Alternatively the connection at A-A 1412 may be by telemetry or cellular phone, depending on a user's requirements. The signal from the source 1401 may also be amplified by an amplifier 1402 and used to energize a directional element, such as a laser diode 1403. In select embodiments of the present invention, output 1404 from a laser diode 1403 is coupled via a connector as at C-C 1407, preferably a long optical fiber umbilical cable, to the F.O. cable 103 through a two-way optical connector 1405 such as an optical signal splitter, optical directional coupler, or the like. Any reflected signal 1406 from the F.O. cable 103 is coupled through the two-way optical connection means 1405, e.g., a splitter, optical directional coupler, or the like, to a fast response device 1408 such as a phototransistor or similar device. The output of the fast response device 1408 is amplified by an amplifier 1409 connected to a vertical amplifier, V 1411A, of the oscilloscope 1411. A resulting trace 1411C on the oscilloscope displays the reflections 1406 resulting from the micro-bends 103F along the F.O. cable 103 as well as any stray returns from the cable's termination.

In select embodiments of the present invention, die connection C-C 1407 between a splitter 1405 and the F.O. cable 103 may be implemented by direct connection of the splitter 1405 to the F.O. cable 103, by using a directly-connected short optical fiber connector, or by using a long optical fiber umbilical cable. Alternatively, data may be transmitted to a remote control center via telemetry 106 or cellular phone for processing, analysis, decision making and archiving 109, 110.

The buried optical "sensor" comprises one or more F.O. cables 103 laid either parallel to ported cables 101, 102 or a F.O. cable 103 spirally wrapped about one or both (not shown separately) of the pair of ported cables 101, 102. In select embodiments of the present invention, an opto-electronics package and a multiplexer (not shown separately) are provided and output to an appropriate processor/display 109, 110 as described above. In select embodiments of the present invention the F.O. cable 103 is a 1-mm, step index plastic fiber with a numerical aperture, NA, of 0.51, a core refractive index, $\eta_{co}$, of 1.492, a cladding refractive index, $\eta_{cl}$, of 1.402, and an attenuation of less that about 0.20 dB/m. (Industrial Fiber Optics, Inc. 1999). Other F.O. cables (either plastic or glass) with different characteristics may be used.

In one embodiment of the present invention, data acquisition, processing and display software is written in commercially available objected oriented language. Other convenient or appropriate computer language may be employed. Custom displays 110 or display formats suitable for use on existing CRTs or LCDs may be developed for clear indication of anomalous conditions. Further, an alert function may be programmed into the processor 110 to indicate when the anomalous condition 105 has reached a critical level.

Depending on implementation specifics, select embodiments of the present invention may have the source 1401, amplifiers 1401, 1409, laser diode 1403, splitter 1405 and photo transistor 1408 replaced with an optical power meter (not shown separately) that measures the reflected photonic power present in an optical path. A power meter provides a more sophisticated (and expensive) implementation that monitors the power of both the transmitted and the reflected/refracted optical signal while producing an output proportional to the normalized reflected power.

Tests

Refer to FIG. 12 depicting top A and perspective B line drawings of the test setup for laboratory tests. A rectangular box 1205 having a length, L, much greater that either its width, W, or height, H, was fitted with two ported cables 101, 102 installed at depth, D, from the bottom of the box 1205 and separation, S, between each cable, each cable having their ends exposed outside the box 1205 with the distal ends of each ported cable 101, 102 terminated in a terminating resistor 1203, 1204, respectively. The box 1205 was then filled with soil and various levels of water 1206 added as indicated by the arrow 1207 and the depth, d, to test the operation of the ported coaxial cables 101, 102. An RF pulse generator 1201 was attached to the transmission cable 101 and an oscilloscope 1202 was attached to the receive cable 102 as a receiver, processor and display.

Figure 10:
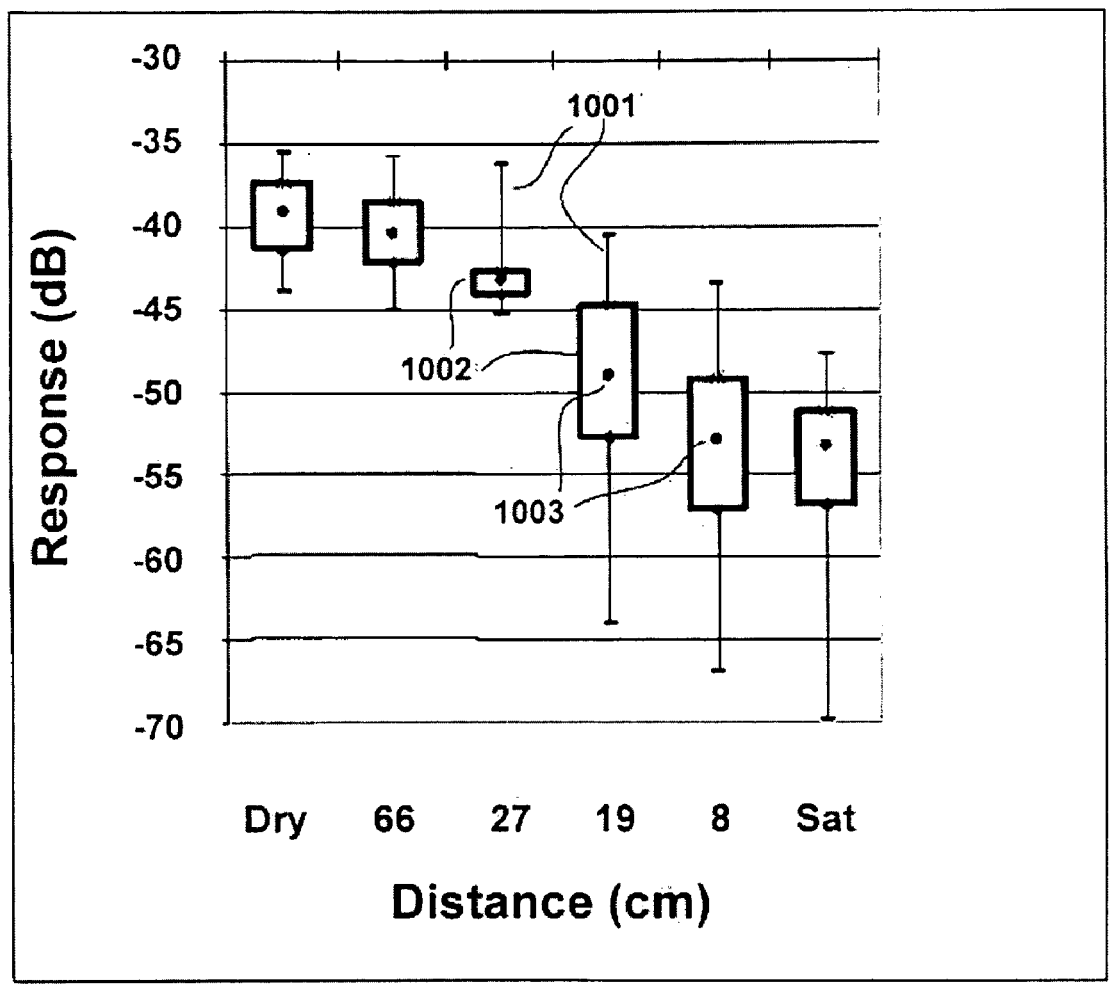
FIG. 10 depicts results from laboratory testing an embodiment of the present invention.

Refer to FIG. 10, summarizing results from laboratory tests of the ported cables 101, 102. The response of the receive cable 102 as displayed on the oscilloscope 1202 is provided on the ordinate in −dB as related to the distance in cm, D-d (FIG. 12), from the ported cables 101, 102 of the water "seepage" (represented by the shaded area 1206). The range of responses of the receive cable 102 to the leakage signal from the transmit cable 101 for each distance, D-d, is that provided by the lines 1001 while the "most likely" response is that shown by the boxes 1002 and the average response is that depicted by the dots 1003. It is evident that as the distance, D-d, decreases to less than 27 cm, the range of responses increases dramatically and "saturation" (D-d=0), is about the same average as for D-d=8 cm but the range of responses for all distances; D-d, less than 27 cm is similar (from 19 cm through saturation). Thus, in addition to the amplitude of the response at the receive cable 102 indicating seepage, the "extended" range of responses may indicate how close to saturation the seepage is becoming.

The abstract of the disclosure is provided to comply with the rules requiring an abstract that will allow a searcher to quickly ascertain the subject matter of the technical disclosure of any patent issued from this disclosure. (37 CFR §1.72 (b)). Any advantages and benefits described may not apply to all embodiments of the invention.

While the invention has been described in terms of some of its embodiments, those skilled in the art will recognize that the invention can be practiced with modifications within die spirit and scope of the appended claims. For example, although the system is described in specific examples for monitoring earthen structures, in particular levees and dams, it may be used for any type of remote monitoring and thus may be useful in such diverse applications as landslide and avalanche warning, bridge and overpass structural monitoring, mining, drilling, remediating, environmental intervention, military operations and the like. Structure monitored may be of any type ranging from naturally occurring to large manmade monoliths. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Thus, it is intended that all matter contained in the foregoing description or shown in the accompanying drawings shall be interpreted as illustrative rather than limiting, and the invention should be defined only in accordance with the following claims and their equivalents.

We claim:

1. A system simultaneously employing complementary techniques to detect and locate hidden anomalies in structure, comprising:
    an RF sub-system comprising:
        at least one pair of transmitter and receiver ported coaxial cables;
        at least one RF source in operable communication with at least said transmitter ported coaxial cable,
        wherein said RF source provides at least one analog signal; and
        at least one RF receiver in operable communication with at least said receiver ported coaxial cable,
        wherein said RF receiver receives at least portions of said analog signal leaked from ports of said ported transmitter coaxial cable as provided by said receiver ported cable;
    an optics sub-system comprising:
        at least one fiber optic cable;
        at least one optical transceiver in operable communication with said at least one fiber optic cable;
        wherein said optical transceiver provides at least one analog optical signal and receives reflections of said analog signal from said fiber optic cable; and
    a control sub-system for at least operating said RF sub-system and said optical sub-system, said control sub-system in operable communication with each of said RF and said optical sub-systems, said control system comprising:
        at least one processor;
        at least one display in operable communication with said at least one processor;
        at least one I/O device in operable communication with at least said processor and said display; and
        at least one communications apparatus in operable communication with at least said I/O device.

2. The system of claim 1, further comprising an alarm in operable communication with said control sub-system.

3. The system of claim 1, said communications apparatus further comprising a telemetry sub-system in operable communication with said control sub-system,
    wherein said telemetry sub-system is in operable communication with at least one cellular phone.

4. The system of claim 1, said RF sub-system further comprising a TDR system in operable communication with at least said control sub-system.

5. The system of claim 4, said TDR system in operable communication with at least said processor, said TDR system comprising:
    at least one RF signal generator for providing said analog signal to at least said ported transmission cable;

a circulator in operable communication with said at least one RF signal generator for coupling said analog signals to said ported transmission cable and coupling leakage signals from said ported transmission cable to said ported receive cable from which said TDR system receives said received leakage signal; and a first algorithm for processing said received leakage signals on said processor and providing results of said processing to at least said display.

6. The system of claim 1, said optical sub-system further comprising an OTDR system in operable communication with said control sub-system.

7. The system of claim 6, said OTDR system comprising:
at least one first amplifier in operable communication with said optical source;
at least one laser diode in operable communication with said at least one first amplifier;
at least one phototransistor;
at least one splitter in operable communication with said laser diode, said fiber optical cable and said phototransistor; and
at least one second amplifier in operable communication with said phototransistor and said display for amplifying the output of said phototransistor prior to submission to said display.

8. The system of claim 1 in which said processor and said display are integral to a personal computer incorporating a monitor.

9. The system of claim 1 in which said display comprises an oscilloscope.

10. The system of claim 1 in which said ported cables incorporate slots having an exterior width in the range of about 1.0 cm to about 2.5 cm and an opening angle of about 5° to about 20°, said slots being spaced apart on each said ported cable about 5 cm to about 30 cm along the length of each said ported cable.

11. The system of claim 1 said fiber optic cable further comprising:
an optical fiber;
a micro-bending inducer in operable communication with said optical fiber; and
a soft resilient armor covering in operable communication with said micro-bending inducer,
wherein said inducer and said covering facilitate the formation of micro-bends in said optical fiber upon impinging of said fiber optic cable by solid media external to said covering.

12. The system of claim 1, said Time Domain Reflectometer comprising at least one RF pulse-modulated reflectometer.

13. The system of claim 12, said at least one RF pulse-modulated reflectometer comprising:
a linear sweep generator for generating said analog signal;
a circulator in operable communication with at least said linear sweep generator for coupling said analog signals from said RF source to said ported transmission cable and coupling said leakage signal from said ported transmission cable to said RF pulse-modulated reflectometer via said ported receive cable and said RF receiver;
a mixer in operable communication with said circulator for combining said at least one received leakage signal with a portion of said transmitted analog signal to yield a first output signal;
a low pass filter in operable communication with said mixer for passing only the low frequency spectra in said first output signal, yielding a second output signal having a frequency spectra in the audio range;
a high pass audio filter in operable communication with said low pass filter for passing only the high frequency spectra of said second output signal, yielding a third output signal having a frequency spectra in the upper end of the audio range;
an audio amplifier in operable communication with said high pass audio filter for amplifying said third output signal, yielding a fourth output signal; and
a processor in operable communication with said audio amplifier for comparing said data on features of said received leakage signal with at least one reference and displaying results of said comparison,
wherein employment of said RF pulse-modulated reflectometer enables alerting to said hidden anomalies.

14. The system of claim 1 in which a single said control sub-system operates multiple said pairs of ported cables and said fiber optic cables by multiplexing said analog RF signals and at least said received leakage signals and by multiplexing said transmitted and reflected optical signals.

15. A method simultaneously employing complementary techniques to detect and locate hidden anomalies in structure, comprising:
providing an RF sub-system comprising:
at least one pair of transmitter and receiver ported coaxial cables;
at least one RF source in operable communication with at least said transmitter ported coaxial cable,
wherein said RF source provides at least one RF analog signal; and
providing at least one RF receiver in operable communication with at least said receiver ported coaxial cable,
wherein said RF receiver receives at least portions of said RF analog signal leaked from ports of said ported transmitter coaxial cable as provided by said receiver ported cable;
providing an optics sub-system comprising:
at least one fiber optic cable;
at least one optical transceiver in operable communication with said at least one fiber optic cable;
providing a control sub-system for at least operating said RF sub-system and said optical sub-system, said control sub-system in operable communication with each of said RF and said optical sub-systems, said control system comprising:
at least one processor:
at least one display in operable communication with said at least one processor;
at least one I/O device in operable communication with at least said processor and said display; and
at least one communications apparatus in operable communication with at least said I/O device;
installing said pairs of ported cables and said fiber optic cables entirely within said structure, paralleling the longitudinal axis of said structure;
connecting said optical sub-system to said fiber optic cable and said control sub-system; connecting said RF sub-system to said ported cables and said control sub-system;
operating said RF sub-system and said optical sub-system to obtain, process, display and archive baseline data; and
operating said system in accordance with user requirements to detect and locate said hidden anomalies by comparing dynamically received data with archived baseline data.

16. The method of claim 15, further comprising employing directional drilling to install said ported cables and said fiber optic cables.

17. The method of claim 15, further comprising providing a telemetry sub-system in operable communication with at least said control sub-system, wherein said telemetry sub-system is in operable communication with a cellular phone.

18. The method of claim 15, integrating a TDR system with said RF sub-system.

19. The method of claim 15, integrating an OTDR system with said optical sub-system.

20. The method of claim 15, integrating said processor and said display in a personal computer incorporating a monitor.

21. The method of claim 15, providing said ported cables with integral slots having a width in the range of about 1.0 cm to about 2.5 cm and an opening angle of about 5° to about 20°, said slots being spaced apart on said fiber optic cable about 5 cm to about 30 cm along the length of said fiber optic cable.

22. The method of claim 15, providing said fiber optic cable as:
   an optical fiber;
   a micro-bending inducer in operable communication with said optical fiber: and
   a soft resilient armor covering in operable communication with said micro-bending inducer,
wherein said inducer and said covering facilitate the formation of micro-bends in said optical fiber upon impinging of said fiber optic cable by solid media external to said covering.

23. The method of claim 15, providing said Time Domain Reflectometer as at least one RF pulse-modulated reflectometer.

24. The method of claim 15, employing a step function with a fast rise time to simulate a pulsed analog RF signal.

25. The method of claim 15, providing said analog signal as a RF pulse-modulated signal on an RF carrier frequency.

26. The method of claim 15 in which said processing further provides at least a measure of the time for a known portion of said optical analog signals to travel from said source end to at least a first location along the length of said fiber optic cable and the at least partial reflection of at least part of said optical signal back to said source end.

27. The method of claim 26, said processing further employing an algorithm to extract at least location of said anomaly along the length of said structure.

28. The method of claim 26 further comparing said at least one feature of said at least one reflection to at least one reference to yield additional information for decision making.

29. The method of claim 26 further providing for digitizing said reflected signal and processing it using a Fast Fourier Transform (FFT) algorithm,
   wherein said processing yields a power spectrum from which location and relative amplitude may be identified and displayed on a computer monitor as said display.

* * * * *